US008608710B2

(12) United States Patent
Zhao

(10) Patent No.: US 8,608,710 B2
(45) Date of Patent: Dec. 17, 2013

(54) PEN NEEDLE ASSEMBLY WITH DIFFERENT GAUGE NEEDLE CANNULAS

(75) Inventor: Ying Zhao, Mahwah, NJ (US)

(73) Assignee: Becton Dickinson & Company, Franklin Lakes, NJ (US)

( * ) Notice: Subject to any disclaimer, the term of this patent is extended or adjusted under 35 U.S.C. 154(b) by 89 days.

(21) Appl. No.: 12/963,849

(22) Filed: Dec. 9, 2010

(65) Prior Publication Data

US 2012/0150128 A1  Jun. 14, 2012

(51) Int. Cl.
*A61M 5/00* (2006.01)
*A61M 5/32* (2006.01)
*A61M 31/00* (2006.01)

(52) U.S. Cl.
USPC ........... 604/240; 604/115; 604/264; 604/272; 604/506

(58) Field of Classification Search
USPC .................... 604/240, 506, 115, 264, 272
See application file for complete search history.

(56) References Cited

U.S. PATENT DOCUMENTS

| 3,884,229 A | 5/1975 | Raines et al. |
| 4,266,543 A | 5/1981 | Blum |
| 5,133,362 A | 7/1992 | Moss |
| 7,556,615 B2 * | 7/2009 | Pettis et al. ................... 604/117 |

FOREIGN PATENT DOCUMENTS

| EP | 0 047 398 A1 | 3/1982 |
| EP | 1 188 456 A1 | 3/2002 |
| WO | 2009/153132 A1 | 12/2009 |

* cited by examiner

*Primary Examiner* — Bhisma Mehta
*Assistant Examiner* — Lauren M Peng
(74) *Attorney, Agent, or Firm* — Hoffmann & Baron, LLP

(57) ABSTRACT

A pen needle assembly is provided herein which includes: a hub having a body with a transverse wall; an arrangement for mounting the hub onto an injector; a first needle cannula extending distally from the transverse wall, the first needle cannula terminating at a distal end, formed for insertion into a patient, with a first lumen extending proximally from the distal end, the first needle cannula being of a first gauge; and, a second needle cannula extending proximally from the transverse wall, the second needle cannula extending from a distal end and terminating at a proximal end with a second lumen extending distally from the proximal end. The first and second lumens are in communication. Further, the second needle cannula is of a second gauge, the second gauge defining a larger external cross-section than the first gauge.

7 Claims, 5 Drawing Sheets

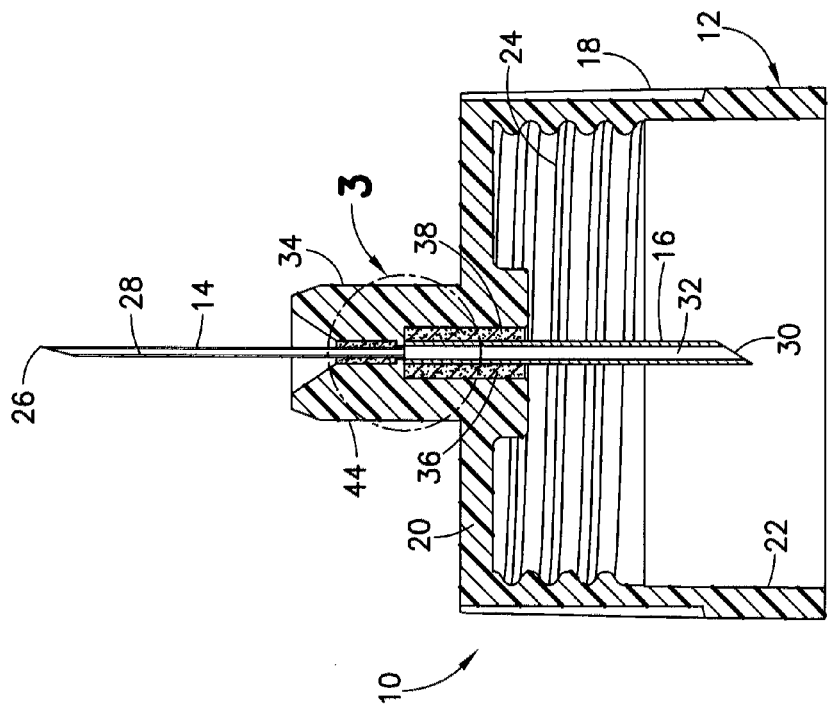
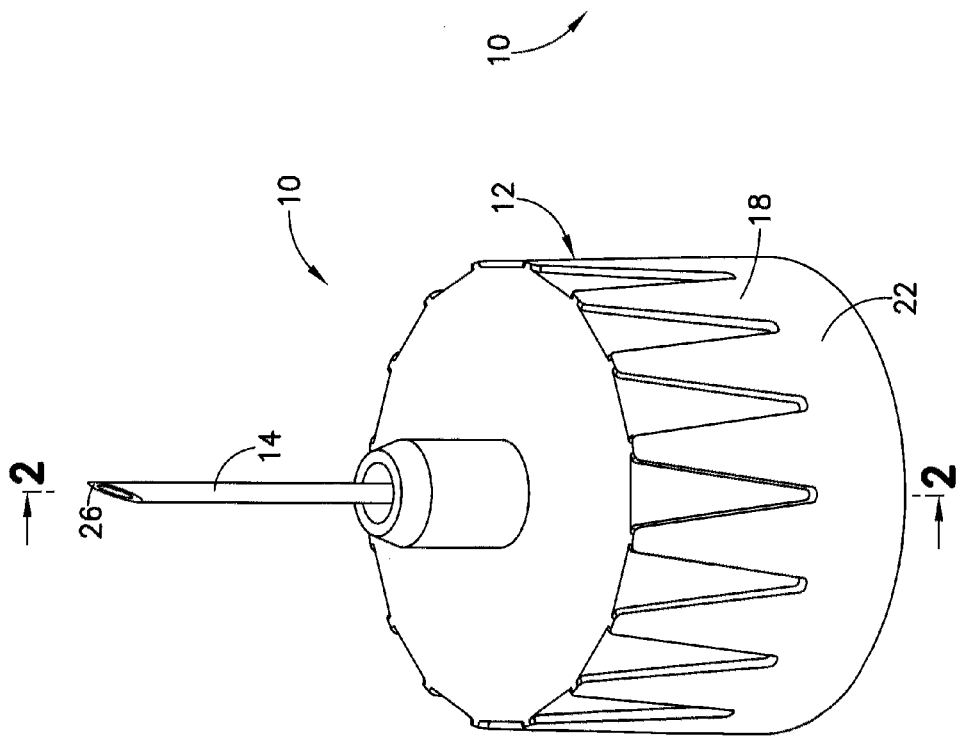

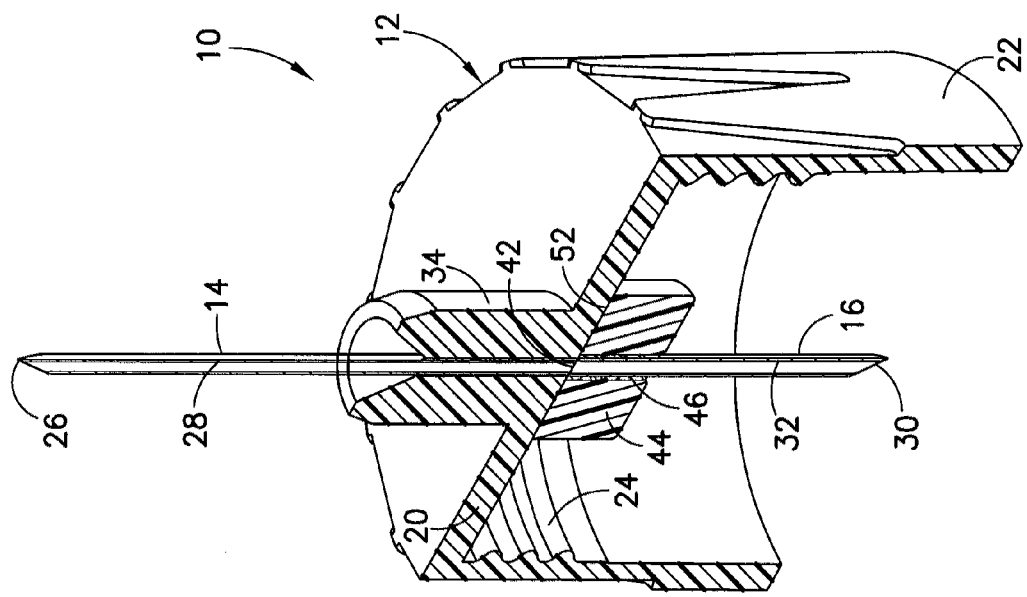

PEN NEEDLE ASSEMBLY WITH DIFFERENT GAUGE NEEDLE CANNULAS

FIELD OF THE INVENTION

This invention relates to pen needle assemblies and, more particularly, to pen needle assemblies having thin gauge needles for injection.

BACKGROUND OF THE INVENTION

Pen needle assemblies are known in the prior art. Typical construction of a pen needle assembly includes a hub to which is fixed a single needle cannula of a particular gauge. The needle cannula includes one end which extends from the hub and is formed for insertion into a patient for injection. This end constitutes a distal end of the needle cannula. The second end of the needle cannula is also exposed and is utilized to come into communication with the contents of a drug cartridge or other reservoir during an injection. This end constitutes a proximal end of the needle cannula. A lumen extends between the proximal and distal ends which provides a flow path for medicament through the needle cannula.

The needle cannula may be of various gauges, resulting in different size external cross-sections. Typically, pen needle assemblies are provided with needle cannulas being in the range of 25-32 gauge. A lower gauge number represents a cross-sectionally larger needle cannula. For example, a needle cannula of 25 gauge will have a larger external cross-section than a needle cannula of 30 gauge. Different gauge needles provide different characteristics (e.g., more buckle resistance, narrower profile, etc.). The entire needle cannula, from proximal end to distal end, is typically formed of a single gauge.

SUMMARY OF THE INVENTION

A pen needle assembly is provided herein which includes: a hub having a body with a transverse wall; an arrangement, disposed on the hub proximally of the transverse wall, for mounting the hub onto an injector; a first needle cannula extending distally from the transverse wall, the first needle cannula terminating at a distal end, formed for insertion into a patient, with a first lumen extending proximally from the distal end, the first needle cannula being of a first gauge; and, a second needle cannula extending proximally from the transverse wall, the second needle cannula extending from a distal end and terminating at a proximal end with a second lumen extending distally from the proximal end. The first and second lumens are in communication. Further, the second needle cannula is of a second gauge, the second gauge defining a larger external cross-section than the first gauge. Advantageously, with the subject invention, two needle cannulas may be arranged in series of different gauges. This permits use of a thinner gauge needle cannula for injection into a patient with a larger gauge, more rigid, needle cannula being provided for accessing a drug cartridge or other reservoir.

As used herein, term "distal", and derivatives thereof, refers to a direction towards a patient during use. The term "proximal", and derivatives thereof, refers to a direction away from a patient during use.

These and other features of the invention will be better understood through a study of the following detailed description and accompanying drawings.

BRIEF DESCRIPTION OF THE DRAWINGS

FIG. 1 is a perspective view of a pen needle assembly formed in accordance with the subject invention;

FIG. 2 is a cross-sectional view taken along line 2-2 of FIG. 1;

FIG. 3 is a enlarged view of Section 3 of FIG. 2;

FIG. 4 is a cross-sectional view of an alternative embodiment of the subject invention;

DETAILED DESCRIPTION OF THE INVENTION

Figure 5:
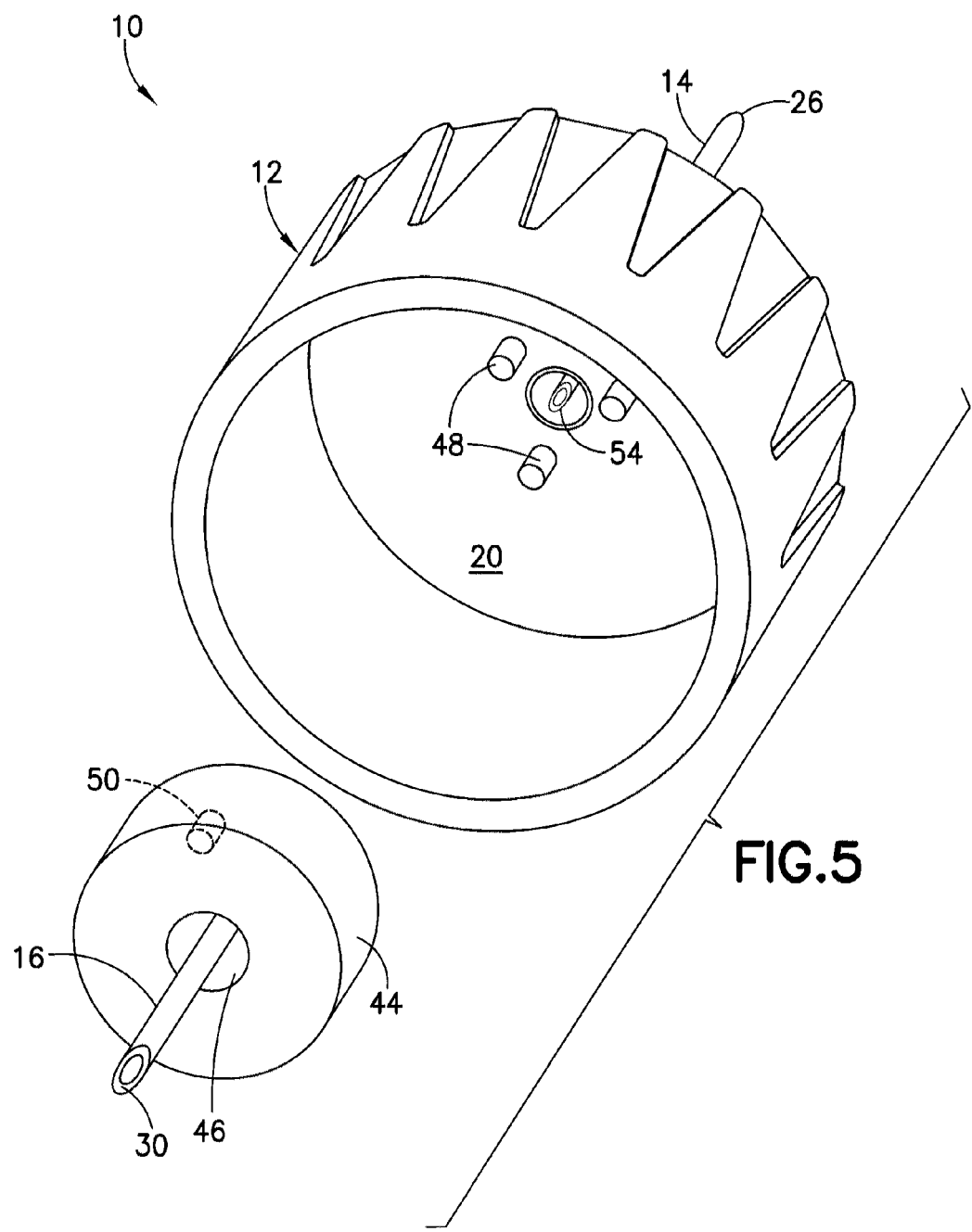
FIG. 5 is an exploded view of the embodiment of FIG. 4.

With reference to the Figures, a pen needle assembly is shown and generally designated with the reference numeral 10. The pen needle assembly 10 generally includes a hub 12, a first needle cannula 14, and a second needle cannula 16. The pen needle assembly 10 is for use with medical injectors, and is particularly well-suited for use with pen injectors.

The hub 12 includes a body 18 having a transverse wall 20 from which extends proximally a skirt 22. In a preferred embodiment, the pen needle assembly 10 is formed to be removably mounted to a medical injector. To this end, features 24 may be disposed on the hub 12, preferably on the skirt 22, for providing mounting onto an injector. The features 24 may include cooperating mechanical elements, such as threads, detents, bayonet-type locking elements, and so forth, and/or surface configurations, such as a tapered Luer surface for frictional engagement. The hub 12 may be formed of a polymeric material, such as a thermoplastic.

The first needle cannula 14 extends distally from the transverse wall 20 and terminates at a distal end 26, which is formed for insertion into a patient. A first lumen 28 is defined in the first needle cannula 14 which extends proximally from the distal end 26.

The second needle cannula 16 extends proximally from the transverse wall 20 and terminates at a proximal end 30. A second lumen 32 is defined within the second needle cannula 16 which extends distally from the proximal end 30.

The first and second needle cannulas 14, 16 are fixed relative to the hub 12 with the first and second lumen 28, 30 being in communication. In this manner, a continuous flow channel is defined from the proximal end 30 to the distal end 26. The first needle cannula 14 extends from the transverse wall 20 a sufficient distance so as to permit injection of the first needle cannula 14 into a patient to a desired depth. The second needle cannula 16 extends a sufficient distance from the transverse wall 20 to ensure that the proximal end 30 may come into communication with the contents of a reservoir or drug cartridge with the pen needle assembly 10 being mounted to an injector. With mounting of the pen needle assembly 10 onto an injector, the second needle cannula 16 will be caused to pierce through a sealing septum or stopper of a drug cartridge or reservoir. The second needle cannula 16 should be provided with sufficient length to obtain complete passage through the sealing septum or stopper with the proximal end 30 accessing the contents of the drug cartridge or reservoir.

The first needle cannula 14 is formed to have a smaller external cross-section than the second needle cannula 16. To this end, the first needle cannula 14 is formed of a first gauge which is different from a second gauge of the second needle cannula 16. The second gauge is selected to provide a larger external cross-section than the first gauge. With this arrangement, the first needle cannula 14, intended for injection into a patient, is provided with a smaller profile than the second needle cannula 16. At the same time, the second needle cannula 16, intended for accessing a drug cartridge or reservoir, provides for a more rigid needle structure which is more resistant to buckling than the first needle cannula 14 when subjected to force applied by a sealing stopper or septum.

In a preferred embodiment, the first needle cannula 14 is a 31 or 32 gauge needle. With the first needle cannula 14 being a 32 gauge needle, it is preferred that the second needle cannula 16 be in the range of 25-31 gauge. Alternatively, with the first needle cannula 14 being a 31 gauge needle, it is preferred that the second needle cannula 16 be in the range of 25-30 gauge. It is noted that regular or reduced wall thickness gauges (e.g., thin wall; extra thin wall; ultra thin wall; micro thin wall) may be utilized. The following is a table setting forth inner and outer diameters of different needle gauges along with nominal wall thicknesses:

TABLE

| Gauge | Wall Type * | Outer Diameter Range (Inches) | Inner Diameter Range (Inches) | Nominal Wall Thickness (Inches) |
|---|---|---|---|---|
| 25 | RW | .0200-.0205 | .0095-.0110 | 0.0050 |
|  | TW | .0200-.0205 | .0115-.0130 | 0.0040 |
|  | ETW | .0200-.0205 | .0135-.0150 | 0.0030 |
|  | UTW | .0200-.0205 | .0155-.0170 | 0.0020 |
|  | MTW | .0200-.0205 | .0175-.0185 | 0.0010 |
| 26 | RW | .0180-.0185 | .0095-.0110 | 0.0040 |
|  | TW | .0180-.0185 | .0115-.0130 | 0.0030 |
|  | ETW | .0180-.0185 | .0130-.0145 | 0.0020 |
|  | UTW | .0180-.0185 | .0145-.0155 | 0.0015 |
|  | MTW | .0180-.0185 | .0155-.0165 | 0.0010 |
| 27 | RW | .0160-.0165 | .0075-.0090 | 0.0040 |
|  | TW | .0160-.0165 | .0095-.0110 | 0.0030 |
|  | ETW | .0160-.0165 | .0115-.0130 | 0.0020 |
|  | UTW | .0160-.0165 | .0130-.0140 | 0.0015 |
|  | MTW | .0160-.0165 | .0140-.0150 | 0.0010 |
| 28 | RW | .0140-.0145 | .0065-.0080 | 0.0035 |
|  | TW | .0140-.0145 | .0085-.0100 | 0.0025 |
|  | ETW | .0140-.0145 | .0100-.0110 | 0.0020 |
|  | UTW | .0140-.0145 | .0110-.0120 | 0.0015 |
|  | MTW | .0140-.0145 | .0120-.0130 | 0.0010 |
| 29 | RW | .0130-.0135 | .0065-.0080 | 0.0035 |
|  | TW | .0130-.0135 | .0080-.0090 | 0.0025 |
|  | ETW | .0130-.0135 | .0090-.0100 | 0.0020 |
|  | UTW | .0130-.0135 | .0100-.0110 | 0.0015 |
|  | MTW | .0130-.0135 | .0110-.0120 | 0.0010 |
| 30 | RW | .0120-.0125 | .0055-.0070 | 0.0030 |
|  | TW | .0120-.0125 | .0070-.0080 | 0.0025 |
|  | ETW | .0120-.0125 | .0080-.0090 | 0.0020 |
|  | UTW | .0120-.0125 | .0090-.0100 | 0.0015 |
|  | MTW | .0120-.0125 | .0100-.0110 | 0.0010 |
| 31 | RW | .0100-.0105 | .0040-.0055 | 0.0025 |
|  | TW | .0100-.0105 | .0055-.0070 | 0.0020 |
|  | ETW | .0100-.0105 | .0070-.0080 | 0.0015 |
|  | UTW | .0100-.0105 | .0080-.0090 | 0.0010 |
| 32 | RW | .0090-.0095 | .0035-.0050 | 0.0025 |
|  | TW | .0090-.0095 | .0050-.0060 | 0.0020 |
|  | ETW | .0090-.0095 | .0060-.0070 | 0.0015 |
|  | UTW | .0090-.0095 | .0070-.0080 | 0.0010 |

Figure 6:
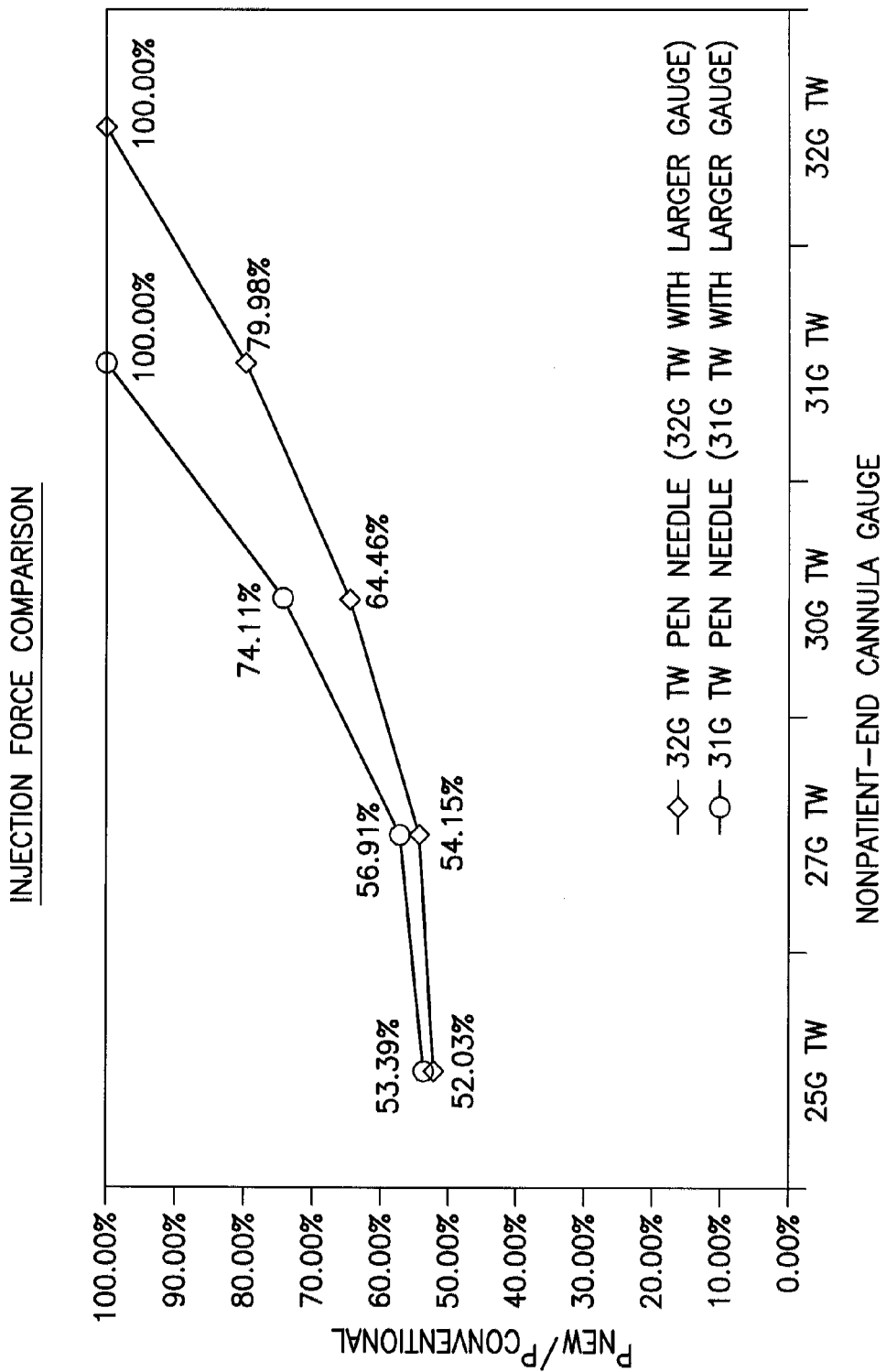
FIG. 6 is a chart depicting an injection force comparison.

*
RW—Regular Wall
TW—Thin Wall
UTW—Ultra Thin Wall
MTW—Micro Thin Wall
ETW—Extra Thin Wall With reference to FIG. 6, a chart is shown representing an injection force comparison. The chart includes two curves, one representing a 31 gauge thin wall needle and a second curve representing a 32 gauge thin wall needle. As shown on the chart, these needle sizes require substantially less injection force as compared to larger needle gauges. For example, a 31 gauge thin wall needle requires 53.39% of the injection force of a 25 gauge thin wall needle, while a 32 gauge thin wall needle requires 52.03% of a 25 gauge thin wall needle.

Figure 7:
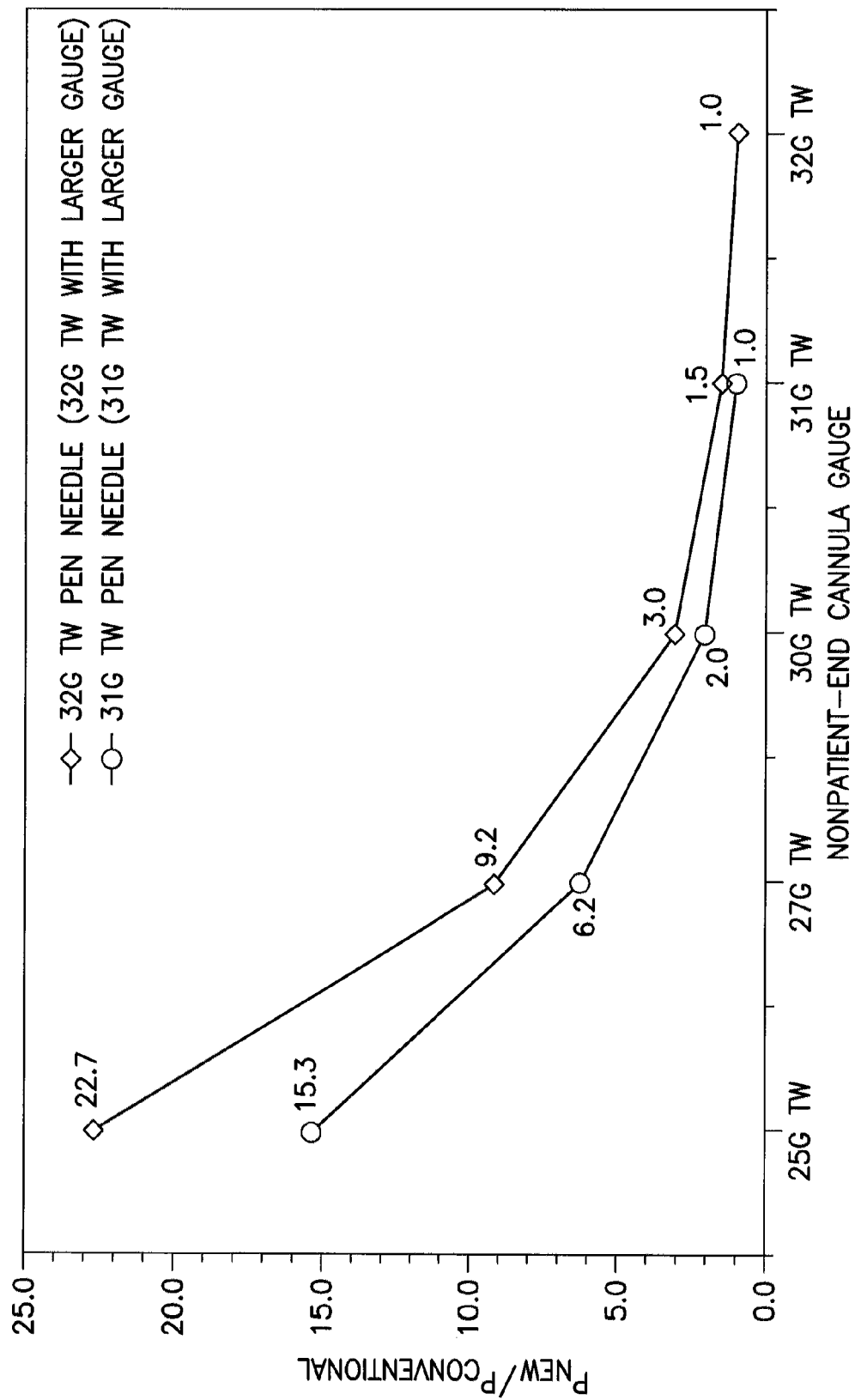
FIG. 7 is a chart depicting a critical buckling force ratio comparison for a non-patient needle cannula.

With reference to FIG. 7, a chart is shown depicting critical buckling force ratios. The chart includes two curves, one representing a 31 gauge thin wall needle and a second curve representing a 32 gauge thin wall needle. As shown in the chart, larger gauge needles provide substantially more buckling resistance than thinner gauge needles. For example, a 25 gauge thin wall needle provides 22.7 times more resistance to buckling than a 32 gauge thin wall needle, while a 25 gauge thin wall needle provides 15.3 times more resistance to buckling than a 31 gauge thin wall needle.

With the subject invention, a pen needle assembly 10 may be provided which advantageously provides good characteristics both for a needle section intended for injection and a needle section intended for accessing contents of a drug reservoir or cartridge. With the use of a thinner gauge for the first needle cannula 14, injection force may be minimized. Also, with the use of a larger gauge for the second needle cannula 16, greater buckling resistance may be provided.

The first and second needle cannulas 14, 16 may be fixed to the hub 12 in any known manner. In a preferred embodiment, as shown in FIGS. 2 and 3, the first and second needle cannulas 14, 16 may be directly fixed to the transverse wall 20. To facilitate such fixation, a collar 34 may be provided which extends longitudinally from the transverse wall 20 and in which is defined a channel 36. The first and second needle cannulas 14, 16 may be fixed in the channel 36 preferably by adhesive 38. Other fixation methods may be used, including insert molding.

With the second needle cannula 16 being of a larger gauge than the first needle cannula 14, the second lumen 32 may be larger than the first lumen 28. With the first and second lumens 28, 32 being in communication, portions 40 of the second lumen 32 may radially extend outwardly from the first needle cannula 14. These portions 40 may be sealed to prevent leakage therefrom, e.g., by use of the adhesive 38 in the channel 36 or the inclusion of a different sealant material.

Preferably, a portion of the transverse wall 20 is located adjacent to a distal end 42 of the second needle cannula 16, as shown in FIG. 3. The transverse wall 20 limits distal movement of the second needle cannula 16 relative to the hub 12. In addition, the transverse wall 20 in this arrangement overlaps the portions 40 of the second lumen 32 which extend radially beyond the first needle cannula 14. This provides a sealing effect and/or an additional sealing effect beyond that provided by the adhesive 38 or other sealant material.

The first and second needle cannulas 14, 16 may be fixed to the hub 12 using other techniques. For example, with reference to FIGS. 4 and 5, the first needle cannula 14 may be fixed to the transverse wall 20 in the same manner as described above, with the second needle cannula 16 being pre-mounted to a mounting collar 44, preferably using adhesive 46. The mounting collar 44 is secured to the transverse wall 20 using any known technique, including adhesion and/or fusion. To enhance securement, cooperating mounting pins 48 on the mounting collar 44 and/or the transverse wall 20 may be utilized which are formed to seat within corresponding mounting apertures 50.

To ensure communication between the first and second lumens 28, 32, the first needle cannula 14 may be positioned so as to be partially inserted into the second needle cannula 16 if corresponding sizing permits. If the first needle cannula 14 cannot be telescoped within the second needle cannula 16, e.g., the second lumen 32 is smaller than the external cross-section of the first needle cannula 14, it is preferred that the first and second needle cannulas 14, 16 meet end-to-end in series with a distal end 42 of the second needle cannula 16 being generally coplanar with a plane within a proximal end 54 of the first needle cannula 14 and with the first and second lumens 28, 32 extending away from the plane. To obtain proper collocation, the distal end 42 of the second needle cannula 16 may be located relative to the hub 12 by interengagement with the transverse wall 20, for example, as shown in FIGS. 2 and 3, or by positioning to be generally coplanar with a distal face 52 of the mounting collar 44. Correspondingly, a proximal end 54 of the first needle cannula 14 may be located to define an interface with the distal end 42 of the second needle cannula 16 by being properly positioned axially within the channel 36. Preferably, the first needle cannula 14 is disposed into the channel 36, prior to assembly with the second needle cannula 16, with a spacer or pin engaging the proximal end 54 to limit the extent of insertion into the channel 36 so that the proximal end 54 is located at a desired position. Subsequently, the second needle cannula 16 is fixed to the hub 12 by either insertion into the channel 36 or by mounting of the mounting collar 44. With mounting of the second needle cannula 16 to the hub 12, the distal end 42 of the second needle cannula 16 may be located to define an interface with the proximal end 54 of the first needle cannula 14.

What is claimed is:

1. A pen needle assembly comprising:

a hub having a body with a transverse wall;

means, disposed on said hub proximally of said transverse wall, for mounting said hub onto an injector;

a first needle cannula extending distally from said transverse wall, said first needle cannula terminating at a distal end, formed for insertion into a patient, with a first lumen extending proximally from said distal end, said first needle cannula includes a proximal end, said first needle cannula being of a first gauge; and, a second needle cannula, separate from said first needle cannula, extending proximally from said transverse wall, said second needle cannula terminating at a proximal end with a second lumen extending distally from said proximal end, said second needle cannula includes a distal end, wherein, said proximal end of said first needle cannula being generally coplanar with said distal end of said second needle cannula within a plane, said first and second lumens extending away from said plane with said first and second lumens being in communication, wherein, a portion of said transverse wall is in overlapping interengagement with said distal end of said second needle cannula so as to limit distal movement of said second needle cannula relative to said hub, and, wherein, said second needle cannula being of a second gauge, said second gauge defining a larger external cross-section than said first gauge.

2. A pen needle assembly as in claim 1, wherein said hub includes a skirt extending proximally from said transverse wall.

3. A pen needle assembly as in claim 1, wherein said means for mounting said hub onto an injector being disposed on said skirt.

4. A pen needle assembly as in claim 1, wherein said distal end of said second needle cannula is in sealing contact with said transverse wall.

5. A pen needle assembly as in claim 4, wherein said transverse wall overlapping portions of said second lumen adjacent to said transverse wall which extend radially beyond said first needle cannula.

6. A pen needle assembly as in claim 1, wherein said transverse wall includes a mounting collar.

7. A pen needle assembly as in claim 6, wherein said distal end of said second needle cannula is in interengagement with said transverse wall at a portion of said mounting collar.

* * * * *